US011020320B1

(12) United States Patent
Panda et al.

(10) Patent No.: US 11,020,320 B1
(45) Date of Patent: Jun. 1, 2021

(54) PILL DISPENSER FOR REFRIGERATOR APPLIANCE

(71) Applicant: Haier US Appliance Solutions, Inc., Wilmington, DE (US)

(72) Inventors: Susheel Panda, Telangana (IN); Gaurav Kumar Verma, Hyderabad (IN); Nithin Naga Venkata Yalamanchili, Louisville, KY (US); Srikanth Raavi Venkata, Louisville, KY (US); Rafi Shaik Mahammed, Louisville, KY (US); Abdel Hamad, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 0 days.

(21) Appl. No.: 16/934,182

(22) Filed: Jul. 21, 2020

(51) Int. Cl.
    *A61J 7/04* (2006.01)
    *A61J 7/00* (2006.01)
    *G16H 20/13* (2018.01)
    *G16H 40/67* (2018.01)

(52) U.S. Cl.
     CPC ........... *A61J 7/0481* (2013.01); *A61J 7/0076* (2013.01); *G16H 20/13* (2018.01); *G16H 40/67* (2018.01)

(58) Field of Classification Search
     CPC ...... A61J 7/0481; A61J 7/0076; G16H 20/13; G16H 40/67
     See application file for complete search history.

(56) References Cited

U.S. PATENT DOCUMENTS

| 5,405,048 | A | * | 4/1995 | Rogers | G07F 11/44 221/211 |
| 5,490,610 | A | * | 2/1996 | Pearson | A61G 12/001 221/2 |
| 5,571,258 | A | * | 11/1996 | Pearson | G07F 11/1657 221/211 |
| 6,607,094 | B2 | * | 8/2003 | MacDonald | G07F 11/24 221/121 |
| 8,061,109 | B2 | * | 11/2011 | Freudelsperger | B65B 5/103 53/52 |
| 8,528,610 | B2 | | 9/2013 | Kuehl | |
| 2006/0213921 | A1 | | 9/2006 | Abdulhay | |
| 2016/0042150 | A1 | | 2/2016 | Moloughney | |

* cited by examiner

*Primary Examiner* — Michael Collins
(74) *Attorney, Agent, or Firm* — Dority & Manning, P.A.

(57) ABSTRACT

A pill dispenser includes a housing and a slidable drawer with a dispenser cup therein. A storage cup is fixed within the housing. The pill dispenser also includes a movable probe, a flexible tip on the probe, and a suction pump in fluid communication with the flexible tip. The pill dispenser may be configured for and/or methods of operating the pill dispenser may include rotating the probe a position above the storage cup, translating the probe downward into the storage cup, and activating the suction pump. While the suction pump is active, the probe is translated to the position above the storage cup, rotated to a position above the dispenser cup, and translated downward into the dispenser cup. The suction pump is deactivated when the flexible tip is within the dispenser cup.

20 Claims, 10 Drawing Sheets

PILL DISPENSER FOR REFRIGERATOR APPLIANCE

FIELD OF THE INVENTION

The present subject matter relates generally to automated pill dispensers, and more particularly to automated pill dispensers which are configured to be selectively removably mounted in refrigerator appliances or free-standing, e.g., on a countertop.

BACKGROUND OF THE INVENTION

Refrigerator appliances generally include a cabinet that defines a chilled chamber for receipt of articles for storage, such as food items and pills. In addition, refrigerator appliances include one or more doors rotatably hinged to the cabinet to permit selective access to articles stored in chilled chamber(s). The refrigerator appliances can also include various storage components mounted within the chilled chamber and designed to facilitate storage of articles therein. Such storage components can include racks, bins, shelves, or drawers that receive articles and assist with organizing and arranging of such articles within the chilled chamber.

Over time, a large volume or number of stored items (e.g., food items, medications, vitamins, etc.) can accumulate within the refrigerator's chilled chamber. As stored items accumulate, users of the refrigerator appliance can have difficulty identifying the items located within the refrigerator appliance, particularly smaller items such as bottles containing medication or other pills. Additionally, a user can also have difficulty determining a quantity of certain items within the refrigerator appliance. These difficulties can be magnified and be of greater concern when dealing with items such as medications. Moreover, these difficulties can be magnified if multiple users add/remove items from a common refrigerator appliance. Consequently, the users may accidentally take or forget to take certain items in a timely manner. Additionally or alternatively, some users may be unaware that certain items have been removed or consumed. Thus, users may fail to replace or replenish such items.

Ensuring that a stock of stored items is maintained or replenished and that the stored items are used, e.g., taken or consumed, by the correct person at the correct time is of particular concern with respect to pills, such as medications or supplements.

Accordingly, a pill dispenser with features for selecting and dispensing pills at a predetermined time would be useful. Further, a pill dispenser with features for verifying that a dispensed pill has been taken would be beneficial. Additionally, a pill dispenser which can be conveniently mounted within an existing refrigerator appliance would be useful. Also, a pill dispenser which is selectively usable as a free-standing device, e.g., on a table or countertop without requiring attachment to another appliance, or as an add-on to another appliance such as a refrigerator appliance would be desired.

BRIEF DESCRIPTION OF THE INVENTION

Aspects and advantages of the invention will be set forth in part in the following description, or may be apparent from the description, or may be learned through practice of the invention.

In one exemplary embodiment, a pill dispenser is provided. The pill dispenser includes a housing that defines a lateral direction, a transverse direction, and a vertical direction. The lateral direction, the transverse direction, and the vertical direction are mutually perpendicular. A drawer is slidably mounted in the housing. A dispenser cup is in the drawer. A storage cup is disposed at a fixed location within the housing. A probe is movably mounted within the housing such that the probe is rotatable within a lateral-transverse plane defined by the lateral direction and the transverse direction and the probe is translatable along the vertical direction. A flexible tip is disposed on a distal end of the probe. A suction pump is in fluid communication with the flexible tip through the probe. The pill dispenser also includes a controller. The controller is configured for rotating the probe within the lateral-transverse plane to a position above the storage cup along the vertical direction. The controller is further configured for translating the probe along the vertical direction from the position above the storage cup until the flexible tip is within the storage cup. The controller is also configured for activating the suction pump when the flexible tip is within the storage cup and translating the probe along the vertical direction to the position above the storage cup after activating the suction pump and while the suction pump remains active. The controller is further configured for rotating the probe within the lateral-transverse plane to a position above the dispenser cup along the vertical direction after translating the probe along the vertical direction to the position above the storage cup, translating the probe along the vertical direction from the position above the dispenser cup until the flexible tip is within the dispenser cup, and deactivating the suction pump when the flexible tip is within the dispenser cup.

According to another exemplary embodiment, a method of operating a pill dispenser is provided. The pill dispenser includes a housing defining a lateral direction, a transverse direction, and a vertical direction. The lateral direction, the transverse direction, and the vertical direction are mutually perpendicular. The pill dispenser also includes a drawer slidably mounted in the housing with a dispenser cup in the drawer, and a storage cup disposed at a fixed location within the housing. The method includes rotating a probe of the pill dispenser to a position above the storage cup along the vertical direction. The probe is movably mounted within the housing such that the probe is rotatable within a lateral-transverse plane defined by the lateral direction and the transverse direction. The probe is also translatable along the vertical direction. Rotating the probe of the pill dispenser to the position above the storage cup comprises rotating the probe within the lateral-transverse plane. The method also includes translating the probe along the vertical direction from the position above the storage cup until a flexible tip disposed on a distal end of the probe is within the storage cup and activating a suction pump in fluid communication with the flexible tip through the probe when the flexible tip is within the storage cup. The method further includes translating the probe along the vertical direction to the position above the storage cup after activating the suction pump and while the suction pump remains active. The method then includes rotating the probe within the lateral-transverse plane to a position above the dispenser cup along the vertical direction after translating the probe along the vertical direction to the position above the storage cup and translating the probe along the vertical direction from the position above the dispenser cup until the flexible tip is within the dispenser cup. The suction pump is deactivated when the flexible tip is within the dispenser cup.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

Repeat use of reference characters in the present specification and drawings is intended to represent the same or analogous features or elements of the present invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, terms of approximation, such as "generally," or "about" include values within ten percent greater or less than the stated value. When used in the context of an angle or direction, such terms include within ten degrees greater or less than the stated angle or direction. For example, "generally vertical" includes directions within ten degrees of vertical in any direction, e.g., clockwise or counter-clockwise.

Figure 1:
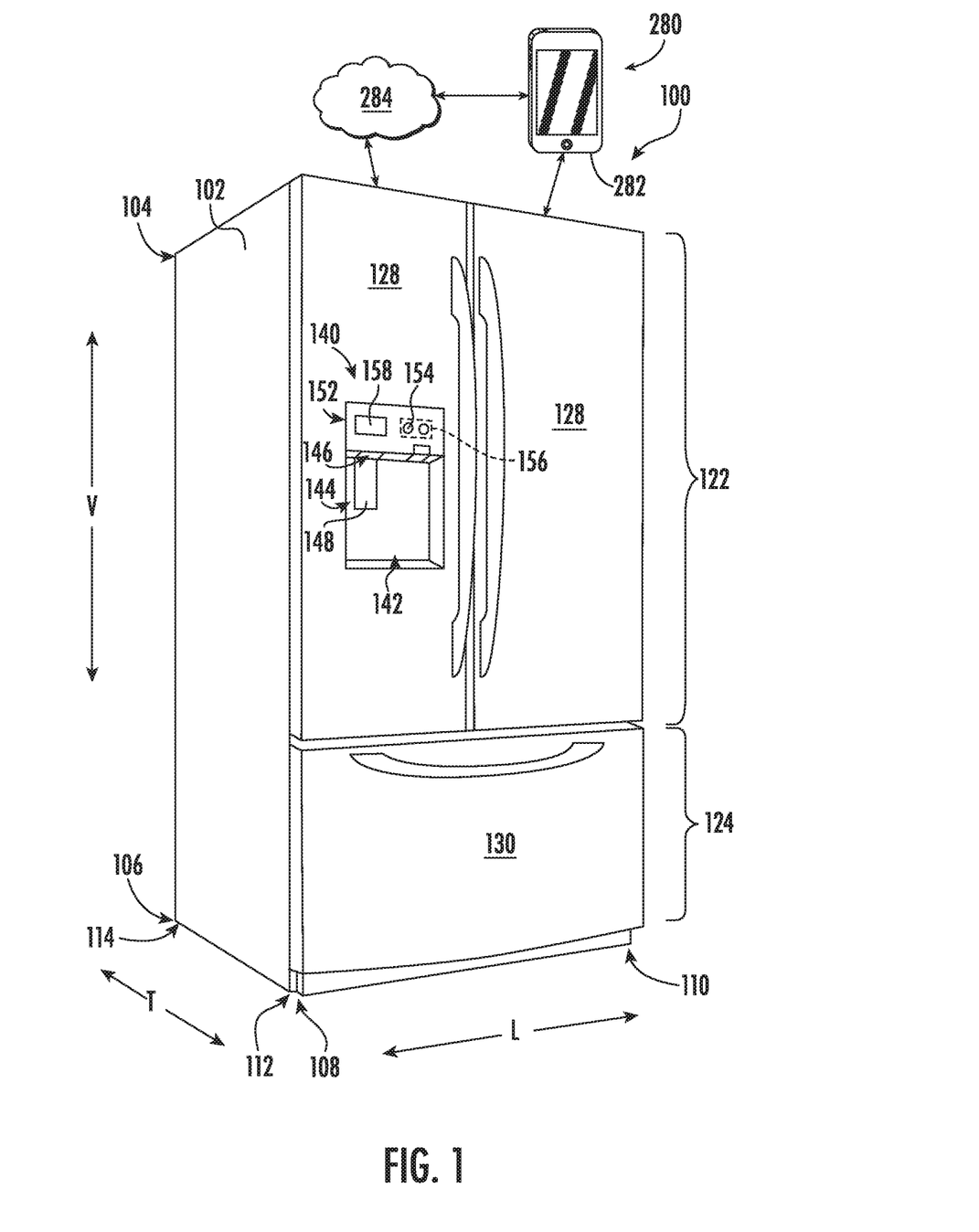
FIG. 1 provides a perspective view of a refrigerator appliance according to an exemplary embodiment of the present subject matter.

FIG. 1 provides a perspective view of a refrigerator appliance 100 in which a pill dispenser according to one or more exemplary embodiments of the present subject matter may be mounted. Refrigerator appliance 100 includes a cabinet or housing 102 that extends between a top 104 and a bottom 106 along a vertical direction V, between a first side 108 and a second side 110 along a lateral direction L, and between a front side 112 and a rear side 114 along a transverse direction T. Each of the vertical direction V, lateral direction L, and transverse direction T are mutually perpendicular to one another.

Housing 102 defines chilled chambers for receipt of food items for storage. In particular, housing 102 defines fresh food chamber 122 positioned at or adjacent top 104 of housing 102 and a freezer chamber 124 arranged at or adjacent bottom 106 of housing 102. As such, refrigerator appliance 100 is generally referred to as a bottom mount refrigerator. It is recognized, however, that the benefits of the present disclosure apply to other types and styles of refrigerator appliances such as, e.g., a top mount refrigerator appliance, a side-by-side style refrigerator appliance, or a single door refrigerator appliance. Consequently, the description set forth herein is for illustrative purposes only and is not intended to be limiting in any aspect to any particular refrigerator appliance or configuration.

Refrigerator doors 128 are rotatably hinged to an edge of housing 102 for selectively accessing fresh food chamber 122. In addition, a freezer door 130 is arranged below refrigerator doors 128 for selectively accessing freezer chamber 124. Freezer door 130 is coupled to a freezer drawer (not shown) slidably mounted within freezer chamber 124. Refrigerator doors 128 and freezer door 130 are shown in the closed configuration in FIG. 1. One skilled in the art will appreciate that other chamber and door configurations are possible and within the scope of the present invention.

Figure 2:
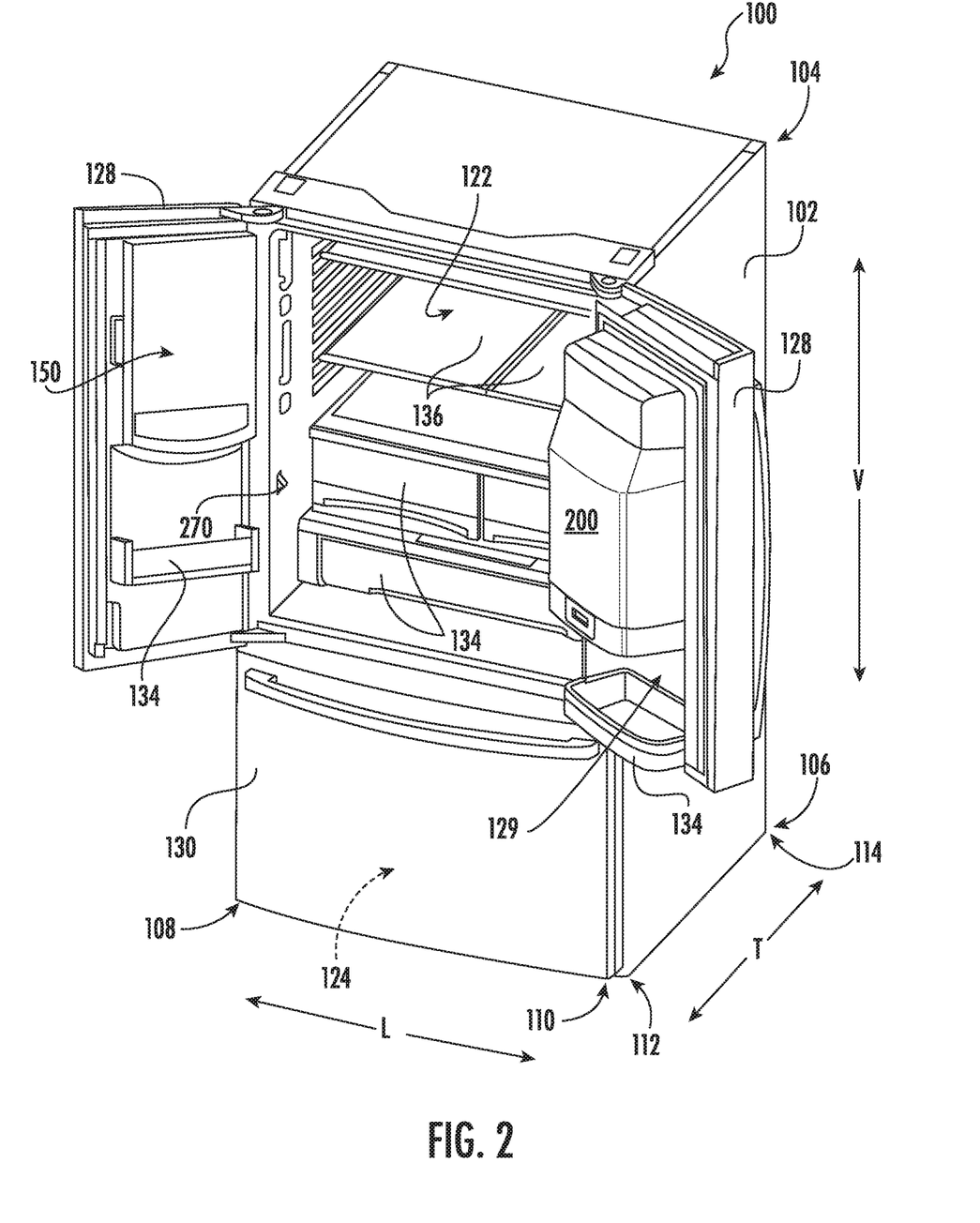
FIG. 2 provides a perspective view of the exemplary refrigerator appliance of FIG. 1, with the doors of the fresh food chamber shown in an open position.

FIG. 2 provides a perspective view of refrigerator appliance 100 shown with refrigerator doors 128 in the open position. As shown in FIG. 2, various storage components are mounted within fresh food chamber 122 to facilitate storage of food items therein as will be understood by those skilled in the art. In particular, the storage components may include bins 134 and shelves 136. Each of these storage components are configured for receipt of food items (e.g., beverages and/or solid food items) and may assist with organizing such food items. As illustrated, bins 134 may be mounted on refrigerator doors 128 or may slide into a receiving space in fresh food chamber 122. It should be appreciated that the illustrated storage components are used only for the purpose of explanation and that other storage components may be used and may have different sizes, shapes, and configurations.

In particular as illustrated in FIG. 2, at least one of the bins 134 may be adjustably mounted on an interior side 129 of one of the doors 128, for example the right door 128 (from the perspective of a user standing in front of the refrigerator 100). For example, the at lease one adjustable bin 134 may be selectively mountable in one of a plurality of vertical positions on the interior side 129 of the right door 128. Further, as will be described in more detail below, in at least some embodiments, a pill dispenser 200 may be removably mounted at one or more of the plurality of vertical positions on the interior side 129 of the right door 128., e.g., the pill dispenser 200 may be used in combination with at least one adjustable bin 134 and/or may be used in place of one or more adjustable bins 134 of a plurality of adjustable bins 134. In particular, in at least some embodiments, the pill dispenser 200 may be mounted in the refrigerator appliance 100 without any additional hardware or changes to the bin mounting structure on the door 128 of the refrigerator appliance 100. That is, in such embodiments, the pill dispenser 200 may be mounted to the interior side 129 of the door 128 simply by replacing one of the bins 134 and the pill dispenser 200 may include the same or similar (compatible) mounting structures as the bins 134, as will be described in more detail below.

Referring again to FIG. 1, a dispensing assembly 140 will be described according to exemplary embodiments of the present subject matter. Although several different exemplary embodiments of dispensing assembly 140 will be illustrated and described, similar reference numerals may be used to refer to similar components and features. Dispensing assembly 140 is generally configured for dispensing liquid water and/or ice. Although an exemplary dispensing assembly 140 is illustrated and described herein, it should be appreciated that variations and modifications may be made to dispensing assembly 140 while remaining within the present subject matter.

Dispensing assembly 140 and its various components may be positioned at least in part within a dispenser recess 142 defined on one of refrigerator doors 128. In this regard, dispenser recess 142 is defined on a front side 112 of refrigerator appliance 100 such that a user may operate dispensing assembly 140 without opening refrigerator door 128. In addition, dispenser recess 142 is positioned at a predetermined elevation convenient for a user to access ice and enabling the user to access ice without the need to bend over. In the exemplary embodiment, dispenser recess 142 is positioned at a level that approximates the chest level of a user.

Dispensing assembly 140 includes an ice dispenser 144 including a discharging outlet 146 for discharging ice from dispensing assembly 140. An actuating mechanism 148, shown as a paddle, is mounted below discharging outlet 146 for operating ice or water dispenser 144. In alternative exemplary embodiments, any suitable actuating mechanism may be used to operate ice dispenser 144. For example, ice dispenser 144 can include a sensor (such as an ultrasonic sensor) or a button rather than the paddle. Discharging outlet 146 and actuating mechanism 148 are an external part of ice dispenser 144 and are mounted in dispenser recess 142. By contrast, refrigerator door 128 may define an icebox compartment 150 (FIG. 2) housing an icemaker and an ice storage bin (not shown) that are configured to supply ice to dispenser recess 142.

A control panel 152 is provided for controlling the mode of operation. For example, control panel 152 includes one or more selector inputs 154, such as knobs, buttons, touchscreen interfaces, etc., such as a water dispensing button and an ice-dispensing button, for selecting a desired mode of operation such as crushed or non-crushed ice. In addition, inputs 154 may be used to specify a fill volume or method of operating dispensing assembly 140. In this regard, inputs 154 may be in communication with a processing device or controller 156. Signals generated in controller 156 operate refrigerator appliance 100 and dispensing assembly 140 in response to selector inputs 154. Additionally, a display 158, such as an indicator light or a screen, may be provided on control panel 152. Display 158 may be in communication with controller 156, and may display information in response to signals from controller 156.

As used to herein, "processing device" or "controller" may refer to one or more microprocessors or semiconductor devices and is not restricted necessarily to a single element. The processing device can be programmed to operate refrigerator appliance 100, dispensing assembly 140 and other components of refrigerator appliance 100. The processing device may include, or be associated with, one or more memory elements (e.g., non-transitory storage media). In some such embodiments, the memory elements include electrically erasable, programmable read only memory (EEPROM). Generally, the memory elements can store information accessible processing device, including instructions that can be executed by processing device. Optionally, the instructions can be software or any set of instructions and/or data that when executed by the processing device, cause the processing device to perform operations.

As shown in FIG. 2, refrigerator appliance 100 may include a door sensor 270 which is generally configured for sensing whether refrigerator door 128 is in the open position or the closed position. For example, door sensor 270 may be a mechanical door switch or a light sensor positioned within fresh food chamber 122 and configured for detecting light when refrigerator door 128 is opened. A controller, e.g., such as appliance controller 156, may be operably coupled to door sensor 270, and may be generally configured for detecting and/or logging when the door 128 is opened, such as when the pill dispenser 200 is accessed or potentially accessed.

Referring again to FIG. 1, a schematic diagram of an external communication system 280 will be described according to an exemplary embodiment of the present subject matter. In general, external communication system 280 is configured for enabling communication between a user, an appliance, and a remote server or network. Specifically, according to the illustrated embodiment, refrigerator appliance 100 and/or pill dispenser 200 may communicate with a remote user interface device 282 either directly (e.g., through a local area network (LAN), Wi-Fi, Bluetooth, etc.) or indirectly (e.g., via a network 284), as well as with a remote server (not shown), e.g., to receive notifications, provide confirmations, input operational data, provide position parameters, etc.

In general, remote user interface device 282 may be any suitable device with a user interface such as a touch screen and/or mechanical buttons/keys, e.g., for providing and/or receiving communications or commands from a user. In this regard, remote user interface device 282 may include, for example, a personal phone, a tablet, a laptop computer, or another mobile device. In addition, or alternatively, communication between the appliance and the user may be achieved directly through an appliance control panel (e.g., control panel 152).

In general, network 284 can be any type of communication network. For example, network 284 can include one or more of a wireless network, a wired network, a personal area network, a local area network, a wide area network, the internet, a cellular network, etc. In general, communication with network may use any of a variety of communication protocols (e.g., TCP/IP, HTTP, SMTP, FTP), encodings or formats (e.g. HTML, XML), and/or protection schemes (e.g., VPN, secure HTTP, SSL).

External communication system 280 is described herein according to an exemplary embodiment of the present subject matter. However, it should be appreciated that the exemplary functions and configurations of external communication system 280 provided herein are used only as examples to facilitate description of aspects of the present subject matter. System configurations may vary, other communication devices may be used to communicate directly or indirectly with one or more appliances, other communication protocols and steps may be implemented, etc. These variations and modifications are contemplated as within the scope of the present subject matter.

In addition, the refrigerator 100 and/or pill dispenser 200 may be operably coupled to a remote user interface device 282 to facilitate improved operation. In this regard, for example, pill dispenser 200 may be Wi-Fi enabled (e.g., via a dedicated controller or wireless communication module in the pill dispenser 200) such that it may communicate with a remote device such as the remote user interface device 282.

Figure 3:
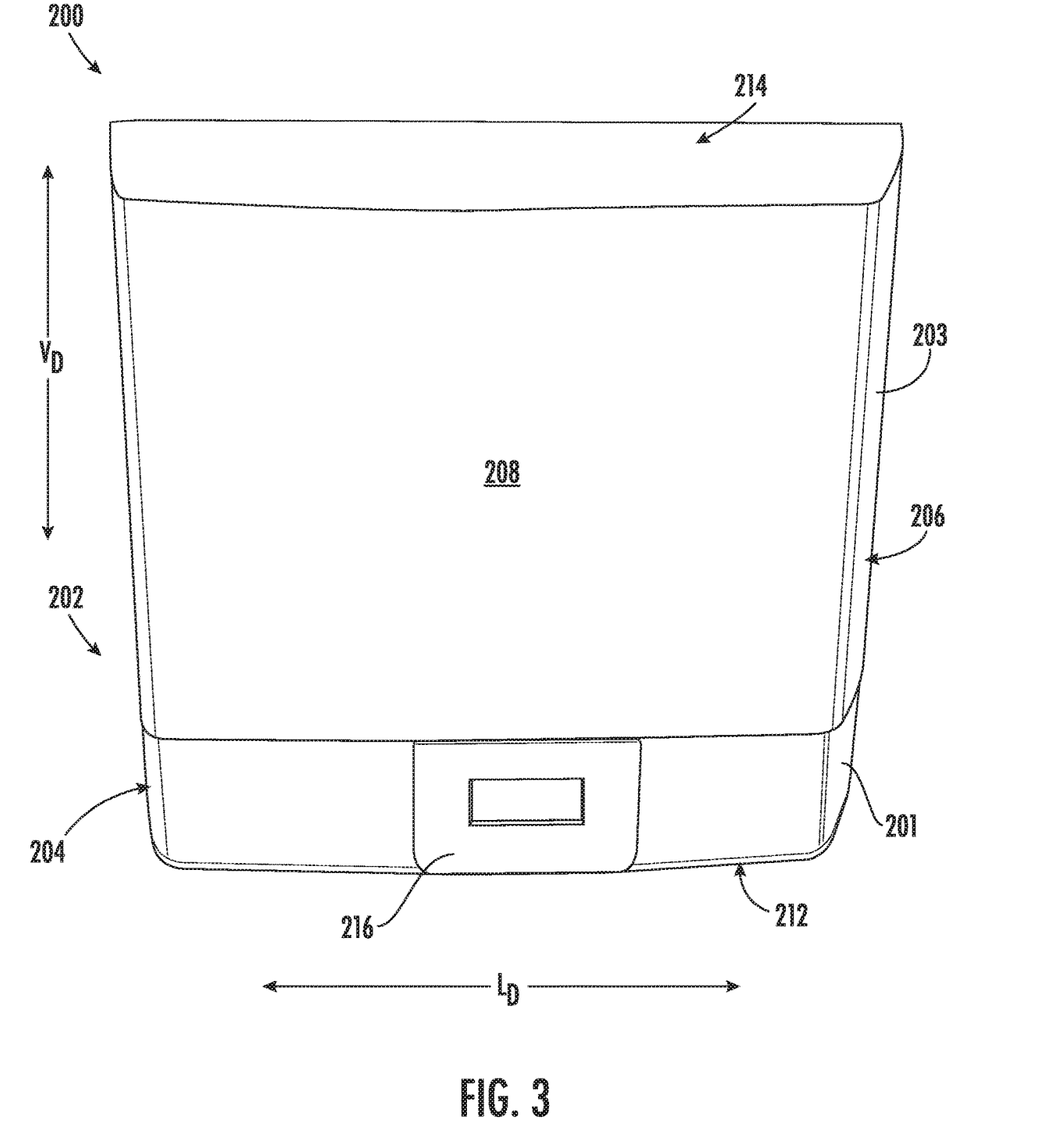
FIG. 3 provides a front view of a pill dispenser that may be selectively removably mounted in the exemplary refrigerator appliance of FIG. 1 according to one or more exemplary embodiments of the present subject matter.
Figure 4:
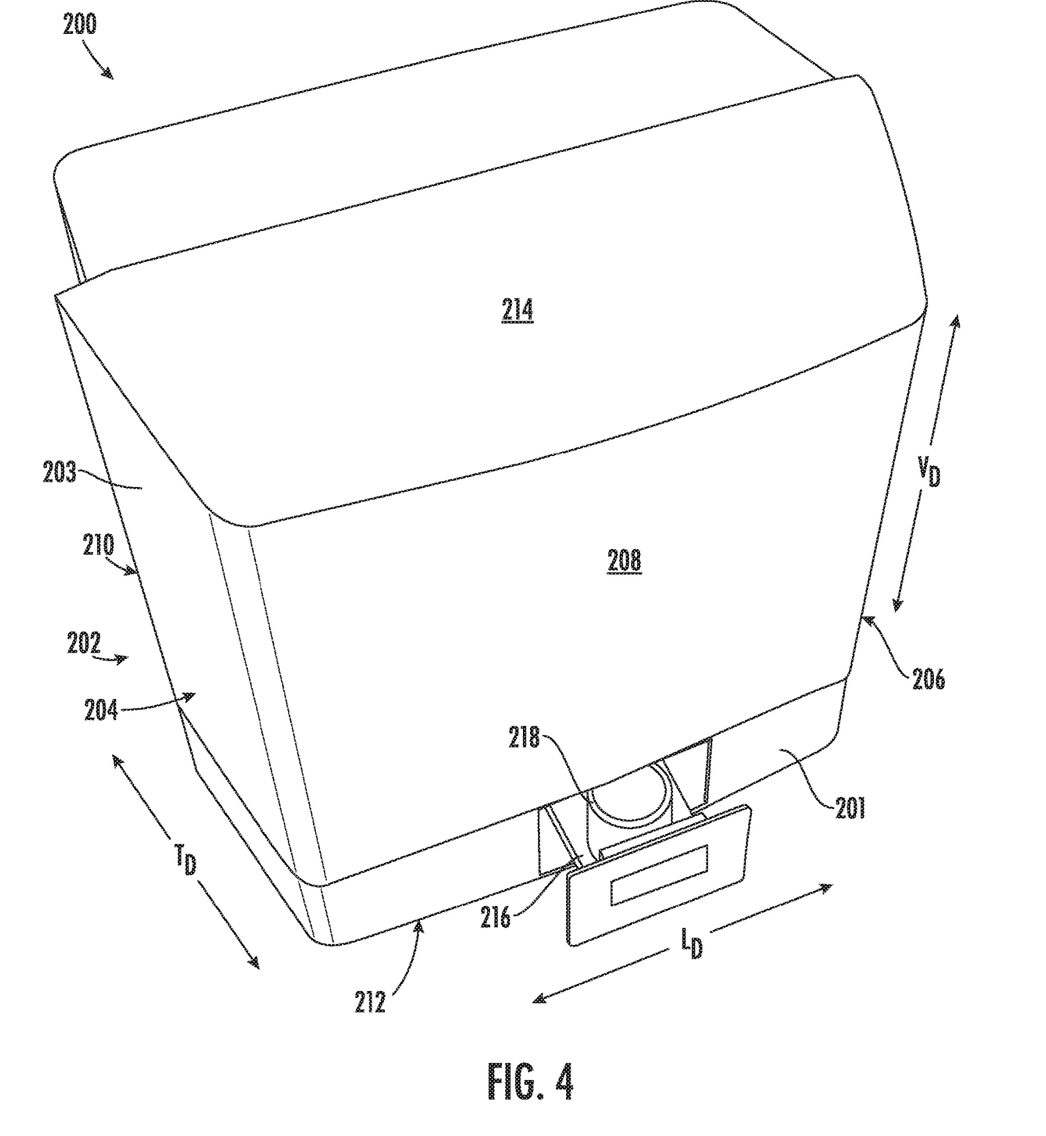
FIG. 4 provides a perspective view of the pill dispenser of FIG. 3.

Turning now to FIGS. 3 and 4, an exemplary pill dispenser 200 according to one or more embodiments of the present invention is illustrated. The pill dispenser 200 may be freestanding, e.g., may be placed on a counter or table, or may be mounted within a refrigerator appliance, such as the example refrigerator 100 described above. In the following description of the pill dispenser 200, reference will be made to the example refrigerator appliance 100 for illustrative purposes only, the pill dispenser 200 may also be usable with various other refrigerator appliances having, for example, a side-by-side configuration, a top mount configuration, differing ice/water dispenser features (or none at all), among numerous other variations in the refrigerator appliance. Accordingly, the pill dispenser 200 is not limited to any particular refrigerator.

As may be seen in FIGS. 3 and 4, the pill dispenser 200 may include a housing 202. The housing 202 may define a lateral direction $L_D$, a transverse direction $T_D$, and a vertical direction $V_D$. The lateral direction $L_D$, the transverse direction $T_D$, and the vertical direction $V_D$ may be mutually perpendicular. In embodiments where the pill dispenser 200 is mounted on the door 128 of the refrigerator 100, the lateral direction $L_D$, the transverse direction $T_D$, and the vertical direction $V_D$ defined by the pill dispenser 200 may be respectively aligned with the lateral direction L, transverse direction T, and vertical direction V defined by the refrigerator appliance 100, e.g., when the door 128 is a closed position.

The housing 202 may extend from a left side 204 to a right side 206 along the lateral direction $L_D$, from a front side 208 to a rear side 210 along the transverse direction $T_D$, and from a bottom side 212 to a top side 214 along the vertical direction $V_D$. The pill dispenser 200 may also include a drawer 216 slidably mounted in the housing 202 with a dispenser cup 218 in the drawer 216. For example, as illustrated in FIGS. 3 and 4, in some embodiments, the drawer 216 may be mounted in the front side 208 of the housing 202 and may be slidable along the transverse direction $T_D$. For example, the drawer 216 may be mounted in the center of the front side 208 along the lateral direction $L_D$.

Turning now to FIGS. 5 through 8, the pill dispenser 200 is illustrated in various positions or stages of operation with a portion of the housing 202 removed to more clearly illustrate internal components of the pill dispenser 200. For example, the housing 202 may include a lower portion or base 201 and an upper portion 203 (FIGS. 3 and 4). The upper portion 203 of the housing 202 may be removably attached to the base 201 of the housing 202, such that the upper portion 203 may be removed, e.g., to access one or more storage cup(s) 220 within the housing 202 for refilling the storage cup(s) 220 with pills, as illustrated in FIGS. 5 through 8.

Figure 5:
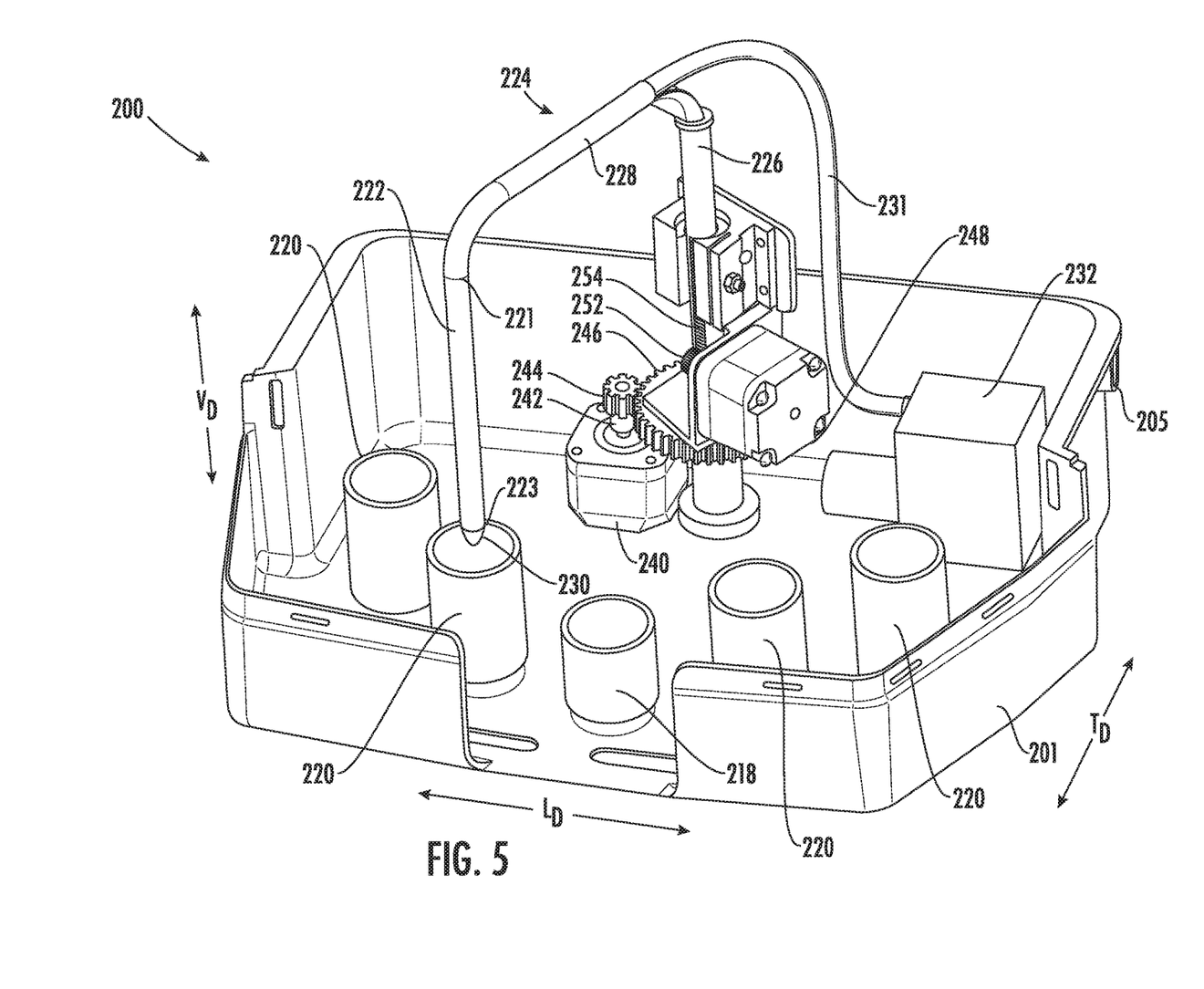
FIG. 5 provides a perspective view of a portion of the pill dispenser of FIG. 3 in a first position.
Figure 7:
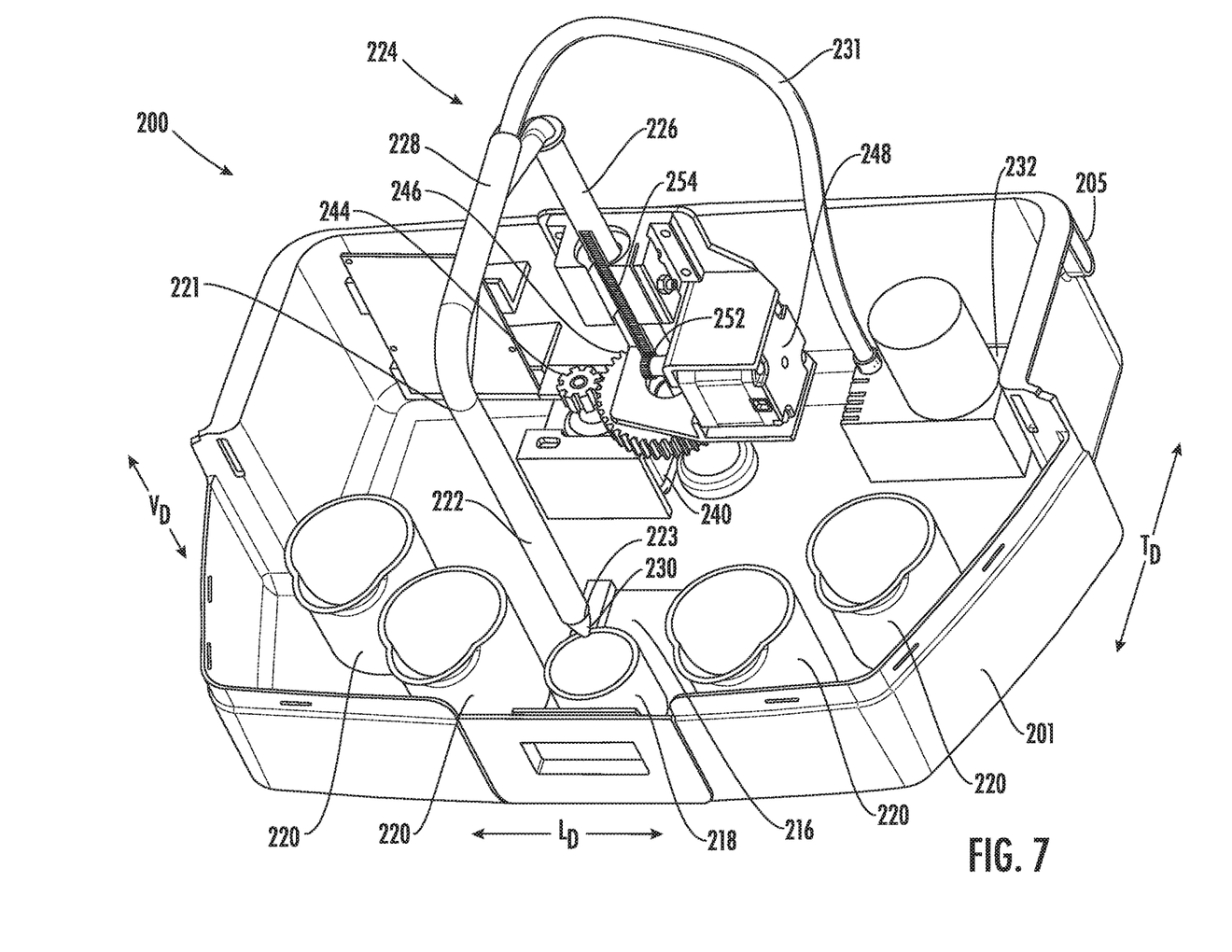
FIG. 7 provides another perspective view of a portion of the pill dispenser of FIG. 3 in a third position.

As mentioned, the pill dispenser 200 may be selectively removably mounted on an interior side 129 of a door 128 of a refrigerator appliance 100. For example, as best seen in FIGS. 5 and 7, the housing 200 may include a tab 205 on an exterior of the housing 200. In some exemplary embodiments, the housing 200 may include two tabs 205 on opposite sides of the housing 201, such as on the left side 204 and the right side 206 which are opposite each other along the lateral direction $L_D$. As will be understood by those of ordinary skill in the art, the tab(s) 205 may be configured for engaging a hook (not shown) on an interior 129 of a door 128 of a refrigerator appliance 100. The hook on the door 128 of the refrigerator appliance may advantageously be the same hook which is used for mounting one of the bins 134, e.g., an adjustable bin 134 as described above. Thus, the pill dispenser 200 may compatible with existing refrigerator appliance 100 and may be used as an add-on accessory to the refrigerator appliance 100 without having to replace the entire refrigerator appliance 100 to obtain the pill dispensing features. Moreover, since the hook is generally understood by those of ordinary skill in the art, it is not specifically illustrated or described in further detail herein for the sake of brevity and clarity.

As may be seen, e.g., in FIGS. 5 through 8, the pill dispenser 200 may include at least one storage cup 220, such as four storage cups 220, each disposed at a fixed location within the housing 202, such as within the base portion 201 of the housing 202, e.g., as illustrated in FIGS. 5 through 8. In some embodiments, the storage cup(s) 220 may be fixedly mounted in the housing 202. For example, the storage cup(s) 220 may be integrally formed with the housing 202. In additional embodiments, each storage cup 220 may be removably mounted in the respective fixed location, and each storage cup 220 may be keyed to a corresponding receptacle in the fixed location within the housing 202. Each storage cup 220 of the plurality of storage cups 220 may be configured to receive and contain a plurality of pills, such as medications. Each storage cup 220 of the plurality of storage cups 220 may store a single medication or type of pill, whereby the pill dispenser 200 may distinguish between types of pills based on the fixed location of the storage cup 220 in which each medication or type of pill is stored.

In some embodiments, e.g., as illustrated in FIGS. 5 and 7, the plurality of storage cups 220 may be aligned with each other and with the dispenser cup 218 within the housing 202. For example, the cups 220 and 218 may be aligned along an arc defined within the lateral-transverse plane. In at least some embodiments, the arc may be circular arc.

The pill dispenser 200 may be configured for and operable to retrieve a pill from a selected one of the storage cups 220 and delivering or depositing the retrieved pill within the dispenser cup 218. Note that the dispenser cup 218 is illustrated in FIG. 5 without the drawer 216 for reference only as to the relative location of the dispenser cup 218 with respect to the storage cups 220 when the drawer 216 is closed. The drawer 216 is omitted from FIG. 5 for illustrative purposes only to avoid obscuring the dispenser cup 218. After the pill dispenser 200 delivers or deposits the retrieved pill within the dispenser cup 218, a user may open the drawer 216 in order to receive the pill from the dispenser cup 218. As will be described in more detail below, the pill dispenser 200 may include features for picking a single pill at a time and for ensuring that only one pill is deposited in the dispenser cup 218 at a time. Thus, the pill dispenser 200 may ensure that a correct medication is dispensed and may ensure that only one medication is dispensed at a time.

In some embodiments, the pill dispenser 200 may include a movable probe 222 which is movably mounted within the housing 202. For example, the probe 222 may be movably mounted within the housing 202 such that the probe 222 is rotatable within a lateral-transverse plane defined by the lateral direction $L_D$ and the transverse direction $T_D$ and the probe 222 is translatable along the vertical direction $V_D$. For example, the probe 222 may rotate within the lateral-transverse plane between the positions illustrated in FIGS. 5 and 7. Also by way of example, the probe 222 may translate along the vertical direction $V_D$ between the positions illustrated in FIGS. 5 and 6, and/or between the positions illustrated in FIGS. 7 and 8.

The probe 222 may extend along the vertical direction $V_D$ from a proximal end 221 to a distal end 223. The proximal end 221 of the probe 222 may be connected to, e.g., integrally formed with, an arm 224. In some embodiments, the arm 224 may include a vertical portion 226 and a second portion 228 that is generally perpendicular to the vertical portion 226, e.g., the second portion 228 may be oriented along one of the lateral direction $L_D$ or the transverse direction $T_D$, and/or may be rotatable between such orientations, such as rotatable within the lateral-transverse plane defined by the lateral direction $L_D$ and the transverse direction $T_D$. The probe 222 may be connected to the second portion 228 of the arm 224 at an opposite end of the second portion 228 from the vertical portion 226 of the arm 224.

The probe 222 may also include a flexible tip 230 which may be disposed on the distal end 223 of the probe 222. For example, the flexible tip 230 may be made of a rubber material, such as silicon rubber, or any other suitable flexible material. The flexible tip 230 may be configured for directly interfacing with (e.g., contacting) the selected pill. For example, the probe 222 may translate along the vertical direction $V_D$ into the selected storage cup 220 until the flexible tip 230 contacts a pill stored therein.

The pill dispenser 200 may also include a vacuum pump or suction pump 232. The suction pump 232 may be in fluid communication with the flexible tip 230. In some embodiments, the suction pump 232 may be in fluid communication with the flexible tip 230 via the probe 222, e.g., the probe 222 may be hollow and the flexible tip 230 may be connected to the suction pump 232 through the probe 222, such as by a flexible tube 231 which extends from the suction pump 232 to the probe 222 in some embodiments, and into the interior of the hollow probe 222 in some embodiments. The tube 231 may be sufficiently flexible to move with the arm 224 while the arm 224 rotates and translates as described. In some embodiments, the flexible tip 230 may be hollow and may include an aperture 234 (FIG. 9) at a distal end (e.g., distal from the remainder of the probe 220) 236 of the flexible tip 230. Thus, a vacuum may be formed within the flexible tip 230 when the flexible tip 230 touches and deforms against a pill, e.g., within the storage cup 220, such that the flexible tip 230 may be sealingly engaged with the pill and the pill may be held in place by the vacuum from the suction pump 232.

In some embodiments, the suction pump 232 may provide a vacuum pressure of between about one-half bar (0.5 bar or 50 kPa) and about one bar (1 bar or 100 kPa), such as between about six-tenths bar (0.6 bar or 60 kPa) and about nine-tenths bar (0.9 bar or 90 kPa), such as about 0.7 bar (70 kPa) or about 0.75 bar (75 kPa). In such embodiments, the suction pump 232 may thereby provide sufficient suction for the probe 222 to carry pills of common sizes from one of the storage cups 220 to the dispenser cup 218 and dispense or deliver such pills to the dispenser cup 281. For example, in embodiments where the suction pump 232 provides about 0.7 bar of pressure, the probe 222 may thereby be usable with (e.g., capable of picking up and carrying) pills ranging in size between about twenty-five hundredths of an inch (0.025") and about sixty hundredths of an inch (0.060").

As mentioned above, the probe 222 may be movable within the housing 202, e.g., rotatable and translatable. In some embodiments, the pill dispenser 200 may include a first motor 240 and a second motor 248. The first motor 240 may be configured for rotating the probe 222 within the lateral-transverse plane and the second motor 248 may be configured for translating the probe 222 along the vertical direction $V_D$.

For example, the first motor 240 may include a drive shaft 242 which is oriented along the vertical direction $V_D$ and which rotates about the vertical direction $V_D$ when the first motor 240 is activated. In some embodiments, the first motor 240 may be coupled to the probe 222 whereby the first motor 240 rotates the probe 222 within the lateral-transverse plane when the motor 240 is activated. For example, the rotation of the drive shaft 242 may be transferred to the probe 222 by a drive gear 244 which is mounted on the drive shaft 242 and a reduction gear 246 which is directly connected to the arm 224, where the arm 224 is directly connected to the probe 222.

In some embodiments, the second motor 248 may include a drive shaft 250 which is oriented perpendicular to the vertical direction $V_D$. The second motor 248 may be coupled to the probe 222 such that the second motor 248 translates the probe 222 along the vertical direction $V_D$ when the second motor 248 is activated. For example, the second motor 248 may be coupled to the probe 222 by a rack and pinion to transfer rotation of the drive shaft 250 into linear movement of the arm 224, and the probe 222 connected thereto, along the vertical direction $V_D$. As illustrated in FIGS. 5 through 8, the rack and pinion may include a drive gear 252 mounted directly on the drive shaft 250 of the second motor 248 and a rack 254 mounted directly on the arm 224, such as on the vertical portion 226 thereof.

Figure 6:
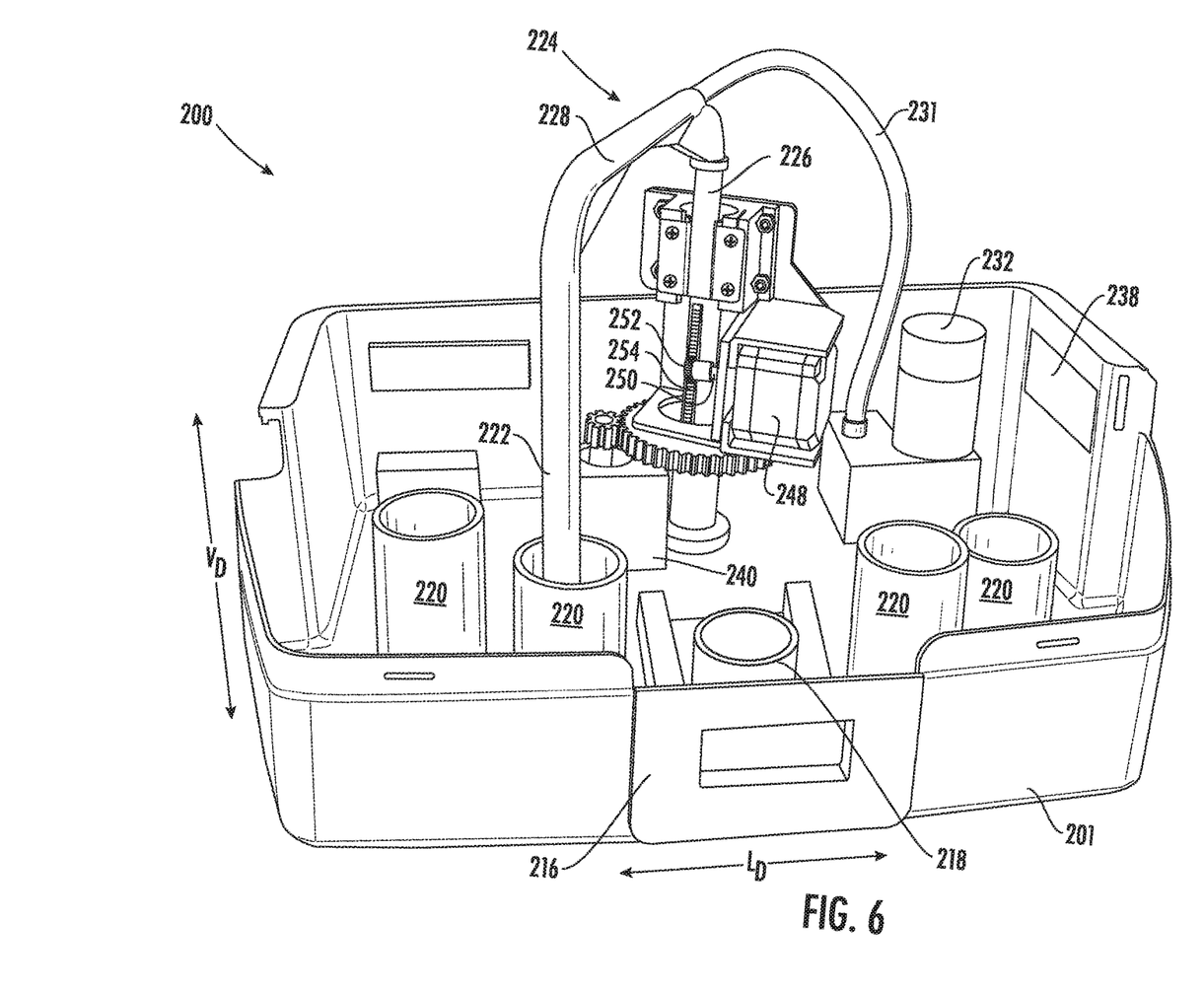
FIG. 6 provides another perspective view of a portion of the pill dispenser of FIG. 3 in a second position.
Figure 8:
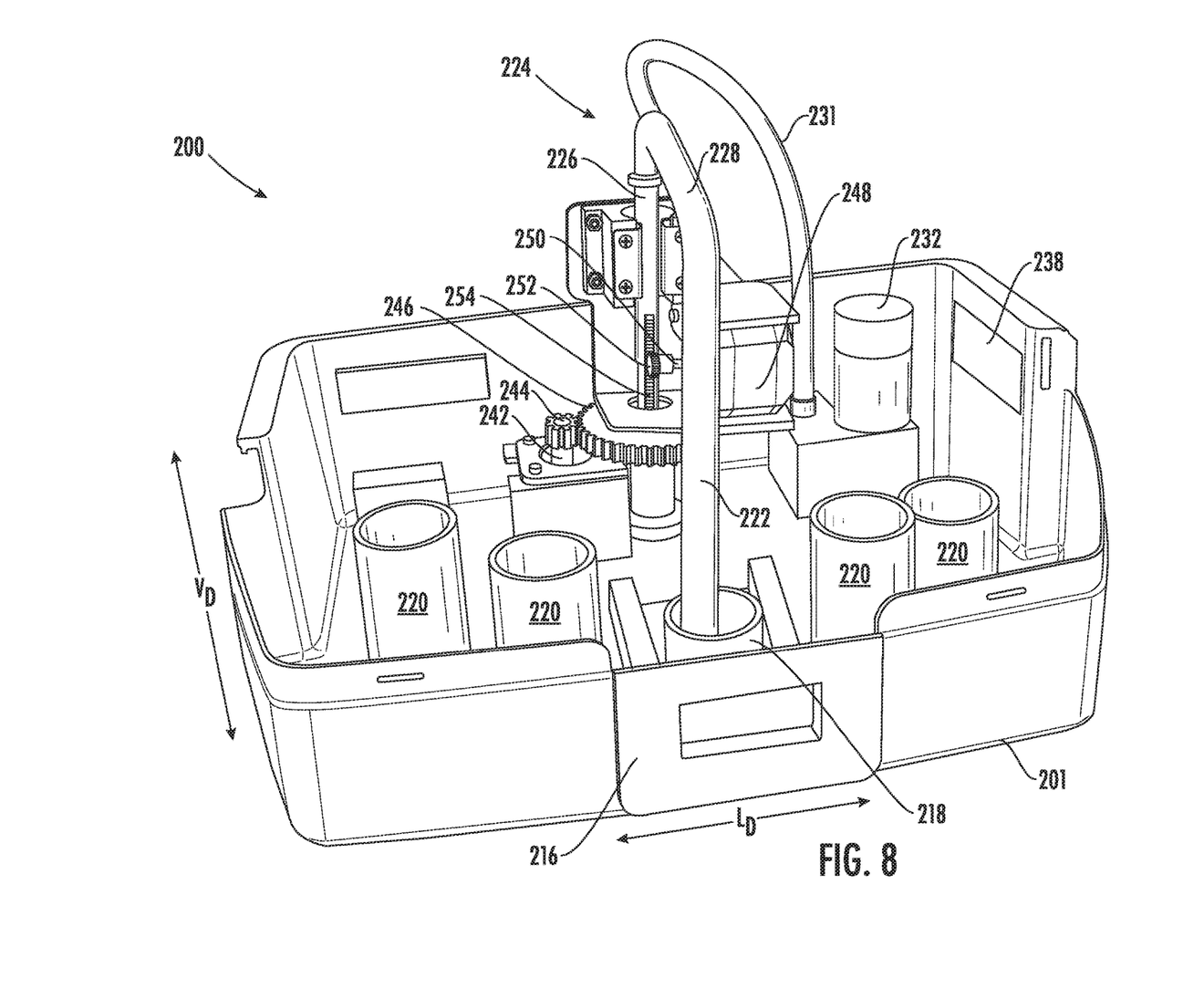
FIG. 8 provides another perspective view of a portion of the pill dispenser of FIG. 3 in a fourth position.

As illustrated for example in FIGS. 6 and 8, the pill dispenser 200 may include a controller 238. The controller 238 may be in operative communication with various other components of the pill dispenser 200, such as the first motor 240, the second motor 248, and the suction pump 232. Similar to the controller 156 of the refrigerator appliance 100 described above, the controller 238 of the pill dispenser 200 may include one or more processing devices or controllers as described above with regard to the controller 156.

Embodiments of the present disclosure may also include methods of operating the pill dispenser 200, examples of which will be described in more detail below. Such methods generally include retrieving a pill from a selected one of the plurality of the storage cups 220 and placing the retrieved pill in the dispenser cup 218. Such methods may also advantageously include determining that the dispenser cup 218 is empty before retrieving and placing the pill, e.g., to reduce or prevent mixing medications. As will be described in more detail below, retrieving the pill may include rotating the probe 222 to a position above, such as directly above a geometric center of, the selected storage cup 220, such as the position illustrated in FIG. 5. This may be followed by translating the probe 222 along the vertical direction $V_D$, e.g., downward, until at least the tip 230 is within the selected storage cup 220, such as the position illustrated in FIG. 6. For example, the probe 222 may be translated vertically downward until a sensor 256 (FIG. 9) in the tip 230 detects that the flexible tip 230 has deformed, e.g., due to contact with a pill within the selected storage cup 220 and/or until the probe 222 reaches a bottommost vertical position which corresponds to the bottom of the storage cup 220. In the latter case, the probe 220 reaching the bottommost vertical position without the tip 230 encountering a pill within the storage cup 220 may indicate that the storage cup 220 is empty. In various embodiments, the empty storage cup 220 condition may be detected or indicated based on the probe 222 reaching a bottommost or lowest vertical position in the probe 222 range of motion along the vertical direction $V_D$ and/or based on the flexible tip 230 deforming due to contact with the bottom inside surface of the storage cup 220. When the storage cup 220 is empty, methods of operating the pill dispenser 200 may include and/or the controller 238 may be configured for sending a reminder or notification, e.g., to a user interface such as a user interface provided on a remote user interface device, such as a notification to refill the storage cup 220. In the former case, the suction pump 232 may be activated when the sensor 256 indicates that the tip 230 has contacted, e.g., is sealingly engaged with, the pill, whereby the suction force holds the pill against the flexible tip 230. After activating the suction pump 232, the suction pump 232 remains active until the pill is placed in the dispenser cup 218. Placing the pill in the dispenser cup 218 may include translating the probe 222 upward along the vertical direction $V_D$ until the tip 230 (and the pill held thereon by the suction pump 232) is clear of the storage cup 220, e.g., is above the storage cup 220 along the vertical direction $V_D$, such as returning to the position illustrated in FIG. 5 from the position illustrated in FIG. 6 (although the pill is not specifically illustrated in FIG. 5, it should be understood that the pill would at this point be stuck to the flexible tip 230 by the pressure from the suction pump 232). Returning to the position of FIG. 5 may be followed by rotating the probe 222 within the lateral-transverse plane until the probe 222 is above, e.g., directly above the geometric center of, the dispenser cup 218, e.g., as illustrated in FIG. 7, and then translating the probe 222 downward along the vertical direction $V_D$ until the tip 230 is within the dispenser cup 218, e.g., as illustrated in FIG. 8. When the tip 230 is within the dispenser cup 218, the suction pump 232 may be deactivated to thereby release the pill from the tip 230, thus placing the pill in the dispenser cup 218.

In various embodiments, methods of operating the pill dispenser 200 may include and/or the controller 238 of the pill dispenser 200 may be configured for rotating the probe 222 within the lateral-transverse plane to a position above a selected storage cup 220 of the plurality of storage cups 220 along the vertical direction $V_D$. One example of such position above a storage cup 200 of the plurality of storage cups 220 is illustrated in FIG. 5.

Additionally, methods of operating the pill dispenser 200 may include and/or the controller 238 may be configured for translating the probe 222 along the vertical direction $V_D$ from the position above the storage cup 220 (e.g., FIG. 5) until the flexible tip 230 is within the storage cup 220 (e.g., as illustrated in FIG. 6). As mentioned above, when the flexible tip 230 is within the storage cup 220, the flexible tip 230 may contact and deform against a pill therein, such that the flexible tip 230 seals against the pill. Thus, the method may also include and/or the controller 238 may also be configured for activating the suction pump 232 when the flexible tip 230 is within the storage cup 220, e.g., such that the vacuum or suction within the flexible tip 230 holds the pill in place on the tip 230 of the probe 222. In particular, and as will be described in more detail below, activating the suction pump 232 may be performed after the tip 230 is within the storage cup 220 and a sensor 256 (FIG. 9) in the tip 230 detects a pill, e.g., as opposed to when the sensor 256 detects the bottom of the storage cup 220 when the storage cup 220 is empty, as mentioned above.

Further, methods of operating the pill dispenser 200 may include and/or the controller 238 may be configured for translating the probe 222 along the vertical direction $V_D$ to the position above the storage cup 220 after activating the suction pump 232, and while the suction pump 232 remains active. Methods of operating the pill dispenser 200 may then include and/or the controller 238 may then be configured for rotating the probe 222 within the lateral-transverse plane to a position above the dispenser cup 218 along the vertical direction $V_D$ after translating the probe 222 along the vertical direction $V_D$ to the position above the storage cup 220.

After rotating the probe 222 within the lateral-transverse plane to a position above the dispenser cup 218, methods of operating the pill dispenser 200 may include and/or the controller 238 may be configured for translating the probe 222 along the vertical direction $V_D$ from the position above the dispenser cup 218 until the flexible tip 230 is within the dispenser cup 218. Methods of operating the pill dispenser 200 may then include and/or the controller 238 may then be configured for deactivating the suction pump 222 when the flexible tip 230 is within the dispenser cup 218, thereby releasing the pill from the flexible tip 230 and placing the pill in the dispenser cup 218.

Figure 9:
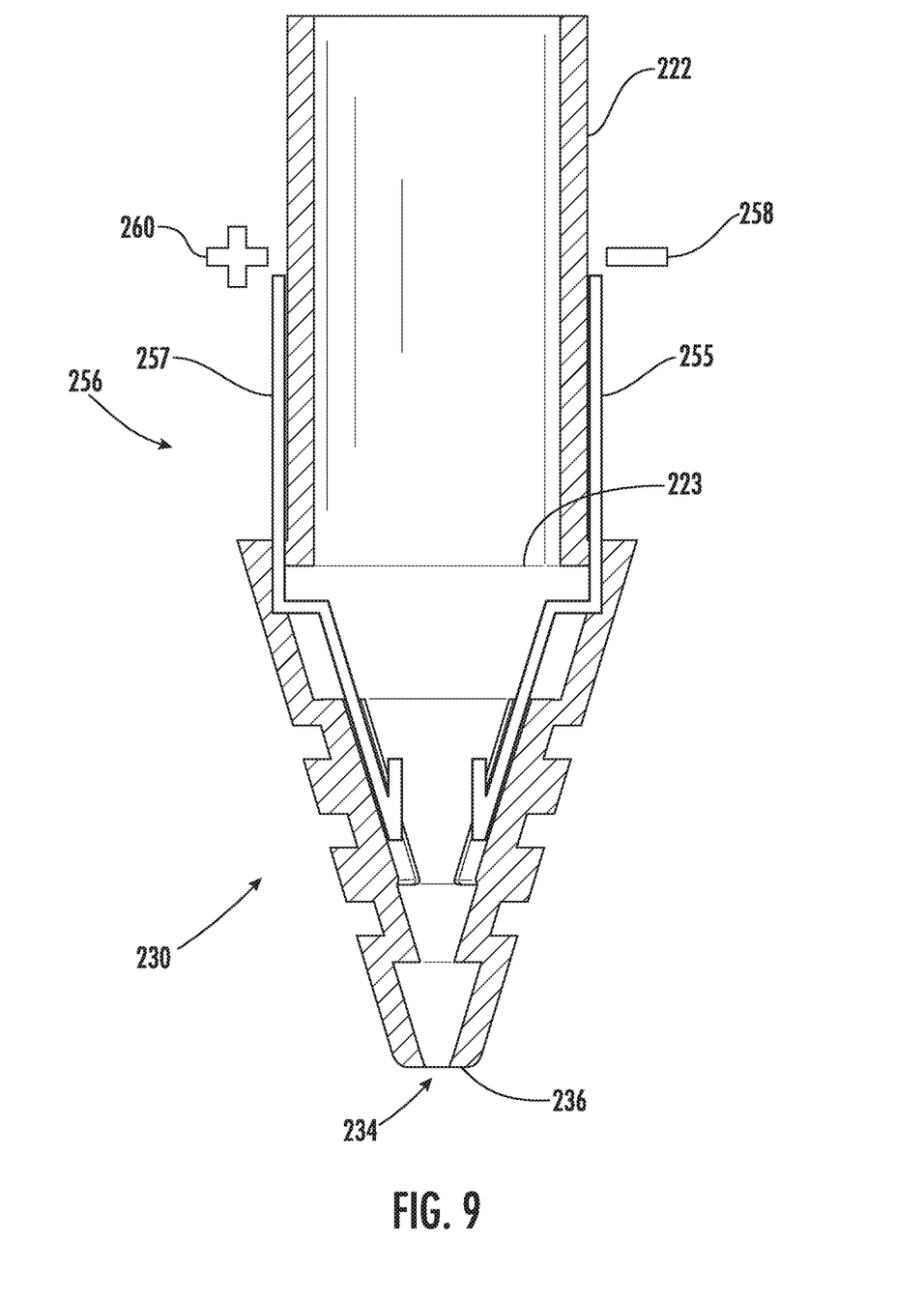
FIG. 9 provides a section view of a tip of a probe for a pill dispenser according to one or more exemplary embodiments of the present subject matter.

Turning now to FIG. 9, as mentioned above, the flexible tip 230 may include a sensor 256 disposed therein. For example, as illustrated in FIG. 9, the sensor 256 may be an electrical sensor including a first lead 255 connected to a negative terminal or anode 258 and a second lead 257 connected to a positive terminal or cathode 260. As illustrated in FIG. 9, each lead 255 and 257 of the sensor 256 may be at least partially embedded in the flexible tip 230 and/or may be disposed within the hollow portion of the flexible tip 230 and in direct contact with an inner surface of the hollow portion of the flexible tip 230. Thus, when the flexible tip 230 flexes or deforms, e.g., biases against and forms a sealing engagement with a pill or compresses against the bottom of the storage cup 220 or dispenser cup 218, the relative positions of the leads 255 and 257 of the sensor 256 with respect to each other changes, which change may be detected based on an associated variation in the electrical properties thereof. Accordingly, the sensor 256 may be operably connected to the controller 238 and the controller 238 may be configured to detect or respond to such variation or change in the electrical properties of the leads 255 and 257 of the sensor 256, and may thereby detect the presence or absence of a pill within one of the storage cups 220 or the dispenser cup 218.

Figure 10:
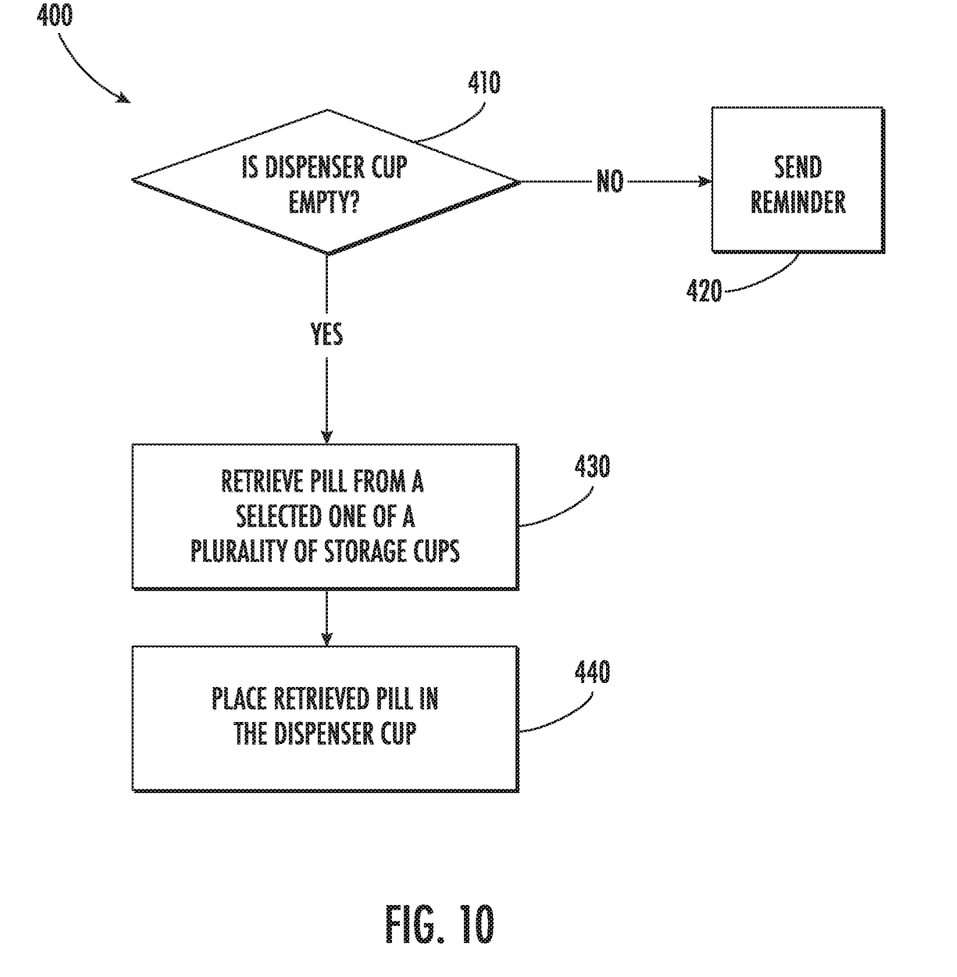
FIG. 10 provides a flow diagram of an example method of operating a pill dispenser according to one or more exemplary embodiments of the present subject matter.

Turning now to FIG. 10, an exemplary method 400 of operating a pill dispenser, such as the pill dispenser 200 described above, according to one or more exemplary embodiments of the present disclosure. As illustrated in FIG. 10, the method 400 may include an initial step 410 of determining whether the dispenser cup 218 is empty. When the dispenser cup 218 is not empty, e.g., when a pill is detected therein, such as by the sensor 256 in the flexible tip 230 of the probe 222, the method 400 may continue at step 420 and send a reminder, such as via one or more user interfaces including on a remote user interface device, e.g., remote user interface device 282 described above, to remind a user to take the medication or other pill which is currently in the dispenser cup 218. In such embodiments, the method 400 may then return to step 410, such as after a suitable time delay, to again verify or detect whether the dispenser cup 218 is empty before proceeding with another pill.

When the dispenser cup 218 is empty, e.g., when the tip 230 of the probe 222 reaches a bottommost position within the dispenser cup 218 without detecting a pill during the probe's travel along the vertical direction $V_D$ from above the dispenser cup 218 to the bottommost position within the dispenser cup 218 and/or when the tip 230 and the sensor 256 therein detect the bottom of the dispenser cup 218, the method 400 may then proceed to step 430 and retrieve a pill from a selected one of the plurality of storage cups 220.

The selection of the one storage cup 220 may be based on a time schedule, e.g., the controller 238 may be programmed with a schedule for when certain medications are to be taken and the controller 238 may include a timer or clock such that the controller 238 performs the method 400 based on a time schedule when the clock indicates that the preprogrammed time has arrived. For example, the controller 238 may be programmed with a time schedule which indicates that medication A stored in a first one of the plurality of storage cups 220 is to be dispensed at time I and that medication B stored in a second one of the plurality of storage cups 220 is to be dispensed at time II (which is later than time I). In such embodiments, the controller 238 may be configured to and/or methods of operating the pill dispenser 200 may include performing the method 400 at time I, including making sure that the dispenser cup 218 is empty at step 410, such as verifying that the previous day's medication has been taken, with the selected one of the plurality of storage cups 220 being the first storage cup in the method 400 at time I, and then performing the method 400 again at time II, which includes verifying that the dispenser cup 218 is empty, e.g., that medication A has been taken, at step 410 and retrieving a pill from the second storage cup 220 when the method 400 is performed at time II.

After retrieving the pill from the selected one of the plurality of storage cups 220 at step 430, the method 400 then proceeds to place the retrieved pill in the dispenser cup 218 at step 440. The steps of retrieving and placing 430 and 440 may include rotating and translating the probe 222 and activating and deactivating the suction pump 232, as described above. Thus, in at least some embodiments, the method 400 may include verifying that the dispenser cup 218 is empty prior to rotating the probe 222 of the pill dispenser 200 to the position above the storage cup 220 along the vertical direction $V_D$.

In some embodiments, the step 410 of verifying that the dispenser cup 218 is empty may include translating the probe 222 downward along the vertical direction $V_D$ from a position directly above the dispenser cup 218 along the vertical direction $V_D$ until the flexible tip 230 of the probe 222 is at a bottommost position within the dispenser cup 218. When the flexible tip 230 reaches the bottommost position without detecting a pill and/or when the bottom of the dispenser cup 218 is detected, the method 400 may then include determining that the dispenser cup 218 is empty. For example, it may be determined that the dispenser cup 218 is empty when a pill is not detected at or above the bottommost position within the dispenser cup 218 during the vertical translation from the position above the dispenser cup 218 to the bottommost position within the dispenser cup 218 and/or when the bottom of the dispenser cup 218 is detected. Further, it may be determined that the dispenser cup is not empty when a pill is detected at or above the bottommost position within the dispenser cup 218 during the vertical translation from the position above the dispenser cup 218 to the bottommost position within the dispenser cup 218.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A pill dispenser comprising:
    a housing defining a lateral direction, a transverse direction, and a vertical direction, the lateral direction, the transverse direction, and the vertical direction being mutually perpendicular;
    a drawer slidably mounted in the housing with a dispenser cup in the drawer;
    a storage cup disposed at a fixed location within the housing;
    a probe movably mounted within the housing whereby the probe is rotatable within a lateral-transverse plane defined by the lateral direction and the transverse direction and translatable along the vertical direction;
    a flexible tip disposed on a distal end of the probe;
    a suction pump in fluid communication with the flexible tip through the probe; and
    a controller, the controller configured for:
        rotating the probe within the lateral-transverse plane to a position above the storage cup along the vertical direction;
        translating the probe along the vertical direction from the position above the storage cup until the flexible tip is within the storage cup;
        activating the suction pump when the flexible tip is within the storage cup;
        translating the probe along the vertical direction to the position above the storage cup after activating the suction pump and while the suction pump remains active;
        rotating the probe within the lateral-transverse plane to a position above the dispenser cup along the vertical direction after translating the probe along the vertical direction to the position above the storage cup;
        translating the probe along the vertical direction from the position above the dispenser cup until the flexible tip is within the dispenser cup; and
        deactivating the suction pump when the flexible tip is within the dispenser cup.

2. The pill dispenser of claim 1, further comprising a sensor disposed in the flexible tip, the sensor in operative communication with the controller, the controller configured for detecting a pill when the sensor indicates deformation of the flexible tip.

3. The pill dispenser of claim 1, wherein the housing is removably mountable on an interior of a door of a refrigerator appliance.

4. The pill dispenser of claim 1, wherein the housing comprises a tab on an exterior of the housing, the tab configured for engaging a hook on an interior of a door of a refrigerator appliance.

5. The pill dispenser of claim 1, further comprising a motor having a drive shaft oriented along the vertical direction, the motor coupled to the probe whereby the motor rotates the probe within the lateral-transverse plane when the motor is activated.

6. The pill dispenser of claim 5, wherein the motor is coupled to the probe by a drive gear on the drive shaft of the motor and a reduction gear connected to the probe.

7. The pill dispenser of claim 1, further comprising a motor having a drive shaft oriented perpendicular to the vertical direction, the motor coupled to the probe whereby the motor translates the probe along the vertical direction when the motor is activated.

8. The pill dispenser of claim 7, wherein the motor is coupled to the probe by a rack and pinion.

9. The pill dispenser of claim 1, wherein the storage cup is one of a plurality of storage cups, the plurality of storage cups aligned with each other and with the dispenser cup within the housing along an arc defined within the lateral-transverse plane.

10. The pill dispenser of claim 9, wherein the arc is a circular arc.

11. The pill dispenser of claim 1, wherein the suction pump is configured to provide a vacuum pressure of about 0.7 bar.

12. A method of operating a pill dispenser, the pill dispenser comprising a housing defining a lateral direction, a transverse direction, and a vertical direction, the lateral direction, the transverse direction, and the vertical direction being mutually perpendicular, a drawer slidably mounted in the housing with a dispenser cup in the drawer, a controller, and a storage cup disposed at a fixed location within the housing, the controller configured to perform the method, the method comprising:
- rotating a probe of the pill dispenser to a position above the storage cup along the vertical direction, the probe movably mounted within the housing whereby the probe is rotatable within a lateral-transverse plane defined by the lateral direction and the transverse direction and translatable along the vertical direction, wherein rotating the probe of the pill dispenser to the position above the storage cup comprises rotating the probe within the lateral-transverse plane;
- translating the probe along the vertical direction from the position above the storage cup until a flexible tip disposed on a distal end of the probe is within the storage cup;
- activating a suction pump in fluid communication with the flexible tip through the probe when the flexible tip is within the storage cup;
- translating the probe along the vertical direction to the position above the storage cup after activating the suction pump and while the suction pump remains active;
- rotating the probe within the lateral-transverse plane to a position above the dispenser cup along the vertical direction after translating the probe along the vertical direction to the position above the storage cup;
- translating the probe along the vertical direction from the position above the dispenser cup until the flexible tip is within the dispenser cup; and
- deactivating the suction pump when the flexible tip is within the dispenser cup.

13. The method of claim 12, wherein the pill dispenser comprises a sensor disposed in the flexible tip, and wherein the method comprises detecting a pill when the sensor indicates deformation of the flexible tip.

14. The method of claim 12, further comprising verifying that the dispenser cup is empty prior to rotating the probe of the pill dispenser to the position above the storage cup along the vertical direction.

15. The method of claim 14, wherein verifying that the dispenser cup is empty comprises translating the probe downward along the vertical direction from a position directly above the dispenser cup along the vertical direction until the flexible tip of the probe is at a bottommost position within the dispenser cup, determining that the dispenser cup is empty when a pill is not detected during the vertical translation at or above the bottommost position within the dispenser cup, and determining that the dispenser cup is not empty when a pill is detected during the vertical translation at or above the bottommost position within the dispenser cup.

16. The method of claim 15, further comprising sending a reminder from the pill dispenser to a remote user device when a pill is detected during the vertical translation at or above the bottommost position within the dispenser cup.

17. The method of claim 12, wherein the storage cup is a second storage cup of a plurality of storage cups, the method further comprising retrieving a first pill from a first storage cup of the plurality of storage cups and placing the first pill in the dispenser cup prior to rotating the probe of the pill dispenser to the position above the second storage cup of the plurality of storage cups along the vertical direction.

18. The method of claim 17, further comprising determining that the dispenser cup is empty after placing the first pill in the dispenser cup and before rotating the probe of the pill dispenser to the position above the second storage cup of the plurality of storage cups along the vertical direction.

19. The method of claim 12, wherein the pill dispenser comprises a sensor disposed in the flexible tip, the method further comprising detecting a pill when the sensor indicates deformation of the flexible tip after the step of translating the probe along the vertical direction from the position above the storage cup until the flexible tip disposed on a distal end of the probe is within the storage cup, wherein the step of activating the suction pump after the step of translating the probe along the vertical direction from the position above the storage cup is performed when the pill is detected, and the method further comprises sending a notification when the pill is not detected during or after the step of translating the probe along the vertical direction from the position above the storage cup until a flexible tip disposed on the distal end of the probe is within the storage cup.

20. The method of claim 12, wherein activating the suction pump comprises providing a vacuum pressure of about 0.7 bar.

* * * * *